United States Patent
Estmer Nilsson et al.

(10) Patent No.: US 9,340,828 B2
(45) Date of Patent: May 17, 2016

(54) PURIFICATION OF NUCLEIC ACID

(71) Applicant: GE HEALTHCARE BIO-SCIENCES AB, Uppsala (SE)

(72) Inventors: Camilla Estmer Nilsson, Uppsala (SE); Johan Ohman, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 14/352,122

(22) PCT Filed: Oct. 25, 2012

(86) PCT No.: PCT/SE2012/051154
§ 371 (c)(1),
(2) Date: Apr. 16, 2014

(87) PCT Pub. No.: WO2013/062476
PCT Pub. Date: May 2, 2013

(65) Prior Publication Data
US 2014/0272999 A1    Sep. 18, 2014

(30) Foreign Application Priority Data

Oct. 27, 2011   (SE) ..................................... 1150999

(51) Int. Cl.
*C12Q 1/68*      (2006.01)
*C07H 21/00*   (2006.01)
*C12N 15/10*   (2006.01)

(52) U.S. Cl.
CPC .......... *C12Q 1/6806* (2013.01); *C12N 15/1006* (2013.01); *C12N 15/1013* (2013.01); *C12N 15/1017* (2013.01)

(58) Field of Classification Search
CPC ......................... C12Q 1/6806; C12N 15/1006
USPC .................................. 435/6.1; 536/25.4, 25.41
See application file for complete search history.

(56) References Cited

U.S. PATENT DOCUMENTS

| 5,523,231 A | 6/1996 | Reeve |
| 5,665,554 A | 9/1997 | Reeve et al. |
| 5,705,628 A | 1/1998 | Hawkins |
| 2003/0008320 A1 | 1/2003 | Baker |
| 2004/0157217 A1 | 8/2004 | Terlesky et al. |
| 2008/0138884 A1 | 6/2008 | Takeshita et al. |
| 2011/0319506 A1* | 12/2011 | Erbacher ............ C12N 15/1006 521/38 |

FOREIGN PATENT DOCUMENTS

| EP | 1 036 082 | 5/2002 |
| EP | 1983051 A2 | 10/2008 |
| WO | 2010072834 A1 | 7/2010 |
| WO | 2013045432 A1 | 4/2013 |

OTHER PUBLICATIONS

European Search Report for European Application No. 12843856 mailed Mar. 11, 2015.
Cao Weidong et al., "Chitosan as a Polymer for pH-Induced DNA Capture in a Totally Aqueous System," Analytical Chemistry, American Chemical Society, US, vol. 78, No. 20, Oct. 15, 2006, pp. 7222-7228.
Chunsheng Xiao et al., "Recent developments in intelligent biomedical polymers," Science in China Series B: Chemistry, vol. 52, No. 2, Feb. 1, 2009, pp. 117-130.

* cited by examiner

*Primary Examiner* — Jezia Riley
(74) *Attorney, Agent, or Firm* — Sutherland Asbill & Brennan LLP

(57) ABSTRACT

The present invention relates to a simple and efficient method to isolate and purify nucleic acids, preferably genomic DNA, from complex samples compared with available methods, by using a ligand which relies on hydrogen bonding to purify the nucleic acids. Preferably the ligand is bound to magnetic beads/particles. More closely the method comprises adding a sample comprising nucleic acid to a polymer having neutral charge; reversibly binding said nucleic acid to said polymer by hydrogen bonding under pH conditions <5; washing said polymer; and eluting said nucleic acid from said polymer under conditions of pH >5. The method is very suitable for sample preparation of nucleic acids, for example for PCR applications.

18 Claims, 1 Drawing Sheet

PURIFICATION OF NUCLEIC ACID

CROSS-REFERENCE TO RELATED APPLICATIONS

This application is a filing under 35 U.S.C. 371 of international application number PCT/SE2012/051154, filed Oct. 25, 2012, published on May 2, 2013 as WO 2013/062476, which claims priority to application number 1150999-9 filed in Sweden on Oct. 27, 2011.

FIELD OF THE INVENTION

The present invention relates to a simple and efficient method to isolate and purify nucleic acids, preferably genomic DNA, from complex samples compared with available methods, by using a ligand which relies on hydrogen bonding to purify the nucleic acids. Preferably the ligand is bound to magnetic beads/particles.

BACKGROUND OF THE INVENTION

U.S. Pat. Nos. 5,665,554 and 5,523,231 describe the use of magnetic beads to isolate total DNA via precipitation. The DNA is precipitated in the presence of magnetic beads that do not specifically associate with the beads. The beads become entrapped within the precipitate and can be used to remove the precipitate without centrifuging.

A different method for purification and isolation of DNA using magnetic beads has been described U.S. Pat. No. 5,705,628. In this method, carboxyl coated magnetic micro particles (1 μm in diameter) are being used to bind DNA non-specifically in the presence of varying concentrations of salt and PEG. The method may selectively bind to nucleic acid of different sizes by adjusting the salt and PEG concentrations.

Yet another method for extracting nucleic acid from biological material is described in EP 1036082. A commercial product used in this method for PCR clean-up is the ChargeSwitch® kit from Invitrogen. According to the manufacturer, this kit includes magnetic beads immobilized with the ChargeSwitch ligand. The ligand appears to have a positive charge at pH<6.5, which becomes neutral at pH>8.5. The protocol is in three steps:
1. The ChargeSwitch® ligand acquires a positive charge at low pH values (<6.5) and binds DNA and RNA through their negatively charged phosphate backbone.
2. Proteins and other impurities can be separated from the ChargeSwitch-bound nucleic acids through the use of aqueous wash buffers.
3. Nucleic acids can then be released from the ChargeSwitch® ligand when the pH of the surrounding media is raised (>8.5) and the positive charge is neutralized.

SUMMARY OF THE INVENTION

The present invention provides an alternative method for purification of nucleic acid comprising adding a sample comprising nucleic acid to a polymer having neutral charge; reversibly binding said nucleic acid to said polymer by hydrogen bonding under pH conditions <5; washing said polymer; and eluting said nucleic acid from said polymer under conditions of pH >5. The method is very suitable for sample preparation of nucleic acids, for example for PCR applications.

Preferably the polymer is polycarboxylated and preferably it comprises 100-500 monomer units.

For example the polymer may be polyacrylic acid, poly lactic acid or carboxymethyldextran. In case of polyacrylic acid a monomer content of 100-500 corresponds to a molecular weight of 7-35 000 Da.

In a preferred embodiment of the method according to the invention the polymers are used as ligands attached to a natural or synthetic solid phase or matrix, such as a bead, particle, membrane, filter, chip, sensor chip, for example a SPR chip, monolith, microfluidic device, pipette tip or any other surface. For example the solid phase may be a bead of agarose, silica or polystyrene or a filter comprising cellulose or PVDF. In one embodiment the solid phase comprises magnetic beads. In another embodiment the solid phase comprises a filter.

In the method according to the invention, the binding of nucleic acid occurs at pH 1-5, preferably pH 2-4, and elution occurs at pH 5-14, preferably pH 7-10.

The nuclei acid may be amplified, such as by PCR, directly after elution. The method of the invention requires no extra steps between elution and amplification since the elution is performed at a suitable pH (pH 8-9) for performing the amplification.

In one embodiment of the method according to the invention the sample comprises nucleic acids of different sizes and thus different hydrogen bonding strength which are separated from each other by adding a solution or flow of a medium affecting hydrogen bonding. This could be done by adjusting the polarity of the solvent during washing or elution using e.g. increasing concentrations of organic solvents, such a methanol, ethanol, that affect the strength of the hydrogen bonding between nucleic acid and ligands, or by the use of other hydrogen bond modifying excipients, such as chaotropic salts, for example urea. Hereby the smallest nucleic acid will be eluted first since their hydrogen bonding to the ligand is weaker than that of larger nucleic acids.

In the method according to the invention the eluted nucleic acids are preferably larger than 200 bp. Thus the invention enables purification of as small nucleic acids or fragments as 200 bp. However, the invention is suitable for a whole range of nucleic acids, such as genomic or plasmid DNA, and is very well suited for genomic nucleic acids of 50-100 kb, or fragments of 10-40 kb, such as 20-30 kb.

One very suitable application for the method according to the invention is then the eluted nucleic acids are 10-40 kb and are used for PCR.

The eluted nucleic acids may be directly sequenced after elution (without amplification).

The nucleic acids purified in the method according may also be used for vaccine applications.

Thus, the present invention relates to methods of isolating biomolecules, in particular isolation of nucleic acids. More specifically, the invention relates to the use of polymers that may form hydrogen bonding with nucleic acids under conditions where the polymers preferably are charge neutral. The isolation can be accomplished by using the polymers as ligands attached to a suitable surface, such as agarose, silica, polystyrene or other solid support. Preferably the polymer ligands can be attached to agarose beads. Suitable polymer ligands may be polycarboxylated such as polyacrylic acid, or carboxymethyldextran of various molecular weights. In one example, the beads will consist of polyCM (carboxymethyl) ligands attached to a magnetic Sepharose® base matrix.

The mechanism for binding of DNA to polyCM magnetic beads is believed to be due to hydrogen bonding between the sugar-phosphate backbone of the DNA with the (protonated) —COOH groups on the polyCM ligand. This hydrogen bonding should be increased at low pH's (DNA binding), but is diminished and reversed at high pH, where the deprotonated —COO⁻ groups will repel DNA (DNA elution).

The poly CM magnetic beads may be used in a variety of applications to:
1. Purify DNA for qPCR (host cell genomic DNA from various cell lines, *E. coli* and Yeast, viral DNA).
2. Purify PCR products for cloning or sequencing.
3. Purify and concentrate DNA to analyse total DNA fragment population. Elution in a small volume concentrates the product from a larger volume giving the benefit to analyse the DNA in a gel format even for samples with low DNA concentration.
4. Size separation of DNA fragments. This may be possible by modifying the hydrogen bonding strength for example by adjusting pH and organic phase concentration e.g. using ethanol or isopropanol.

The demand from regulatory authorities (European Pharmacopoeia) for cell derived vaccines implies that the residual host cell DNA fragments should be <200 bp to exclude possibility of retroviral trans elements. Vaccine manufacturers analyse this today by using extending primer pairs on one or two gene fragments in qPCR.

Using polyCM magnetic beads according to the invention for DNA purification would enable analysis of total DNA fragments even for samples with low DNA concentration (<100 ng/ml)

DETAILED DESCRIPTION OF THE INVENTION

The invention will now be described more closely below in association with some non-limiting examples.

Protocol

Figure 1:
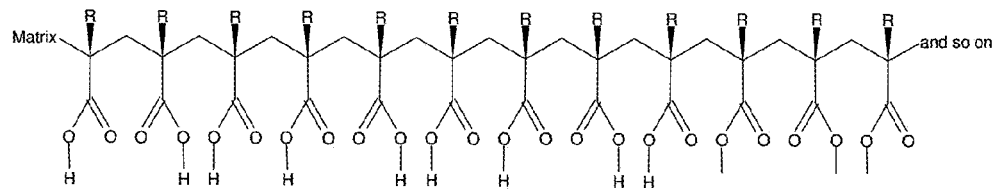
FIG. 1 is an illustration of the poly CM-ligand attached to a matrix. Hydrogen bonding may occur via protonated —COOH groups.

Binding. The polyCM ligand (FIG. 1) interacts with nucleic acids preferably under acidic conditions (pH<5) with increasing strength as the pH is decreased further. The binding is mediated via hydrogen bonds between the ligand and the sugar-phosphate nucleic acid backbone. The use of harsh reagents such as chaotropic salts or organic solvents commonly used may be omitted if preferred, which would be an advantage as these reagents are known to compromise the efficiency of many downstream processes such as PCR. It is also possible to bind and separate nucleic acids of varying lengths, as smaller fragments will require a lower pH for binding compared with larger fragments and the hydrogen-bonding strength may be modified by addition of different concentrations of an organic solvent, e.g. ethanol or isopropanol.

Washing. Washing is preferably done with water with/without addition of harsh reagents to remove proteins and other contaminants.

Elution. Nucleic acids can be released through repulsion from the ligand by simply raising the pH (pH>5). The ligand will become negatively charged (same net-charge as the nucleic acids). It is contemplated that is will be possible to elute nucleic acids with a weak buffer, without additives that may disturb downstream processes such as PCR. This may prove to be highly beneficial compared with standard methodologies.

The benefits with the magnetic bead format will allow the use of very small amount of beads that can be quantitatively recovered. The beads can be used in volumes ranging from 1 μl up to hundreds of μl with ease, making this format useful for devices such as 96-well plates, micro centrifuge tubes (Eppendorf tubes) or other commonly used laboratory plastic-ware. It also allows the user to choose between manual handling and automation using robotics.

EXPERIMENTAL PART

Materials

TABLE 1

Tested gel media

| Gel media | Ligand | Ligand level |
|---|---|---|
| 1 | Carboxy Methyl Cellulose | |
| 2 | Cellulose sulfate | |
| 3 | Hydroxy Ethyl Cellulose | |
| 4 | Carboxy Methyl Dextran | |
| 5 | Poly CM (polyacrylic acid) | Low sub. |
| 6 | Poly CM (polyacrylic acid) | High sub. |
| 7 | Sulfopropyl | |
| 8 | Poly CM (polyacrylic acid) | High sub. |
| 9 | Carboxymethyl | |
| 10 | Aminocaproic acid | |

Synthesis Methods of Gel Media

Mag DNA prototypes have been prepared by allyl activation of Sepharose or Mag Sepharose beads followed by immobilization of different ligands.

Bioreagents and Chemicals

Sonicated Salmon Sperm DNA, 27-4565-01 (GE Healthcare), 100 u, lot K12012

Sonicated Calf Thymus DNA, 27-4563-01, 100 u (units)

1 unit=50 μg DNA. Dissolve 100 u with 10 ml H$_2$O to yield the final concentration of 500 μg/ml Confirm concentration by measurement of UV absorbance on NanoVue plus instrument.

Chemicals

ChargeSwitch Forensic DNA Purification kit, CS11200 (Invitrogen)

Tris-HCl, 2-Amino-2-hydroxymethyl-propane-1,3-diol

Glycine-HCl

MilliQ water

Ethanol

EDTA, Ethylenediaminetetraacetic acid

SDS, Sodium dodecyl sulfate

Methods

UV Absorbance Measurement

UV absorbance was measured on a NanoVue plus instrument to quantitate DNA/RNA and to estimate the purity. Absorbance readings are presented as their normalized 10 mm path length values, to allow the use of literature based factors for concentration measurements. Nucleic acids can be quantified at 260 nm because at this wavelength there is a clearly defined peak maximum. A 50 μg/ml DNA solution, a 40 μg/ml RNA solution and a 33 μg/ml solution of a typical synthetic Oligonucleotide all have an optical density of 1.0 A in a 10 mm path length cell. These factors (50, 40 and 33 respectively) can be inserted into the formula below, although they do vary with base composition and this can be calculated more precisely if the base sequence is known.

Nucleic acids extracted from cells are accompanied by protein and extensive purification is required to remove the protein impurity. The 260/280 nm Absorbance ratio gives an indication of purity, however it is only an indication and not a definitive assessment. Pure DNA and RNA preparations have expected ratios of 1.7-1.9 and ≥2.0 respectively. Deviations from this indicate the presence of impurity in the sample, but care must be taken in the interpretation of results. An elevated Absorbance at 230 nm can also indicate the presence of impurities. 230 nm is near the Absorbance maximum of peptide bonds and may also indicate interference from common buffers such as Tris and EDTA. Background correction at a wavelength well apart from the nucleic acid or protein peaks is often used to compensate for the effects of background absorbance. The procedure can adjust for the effects of turbidity, stray particulates and high-absorbance buffer solutions.

Concentration=(Abs260−Abs320)*Factor

Abs ratio 260/280=(Abs260−Abs320)/(Abs280−Abs320)

Abs ratio 260/230=(Abs260−Abs320)/(Abs230−Abs320)

qPCR

PCR is the most commonly used method for amplifying nucleic acid samples. It has widespread utility in both scientific research and applications such as forensics and clinical work. The most common PCR methods are end-point PCR and real-time or quantitative PCR (qPCR). Either of these can be combined with a reverse transcriptase step (RT-PCR and RT-q PCR, respectively) to enable amplification of RNA.

Nucleic Acid Purification

Standard Workflow for Nucleic Acid Preparation

Lyse sample→Bind DNA→Wash away unbound impurities→Elute bound DNA

Protocol 1

Run according to the user's manual in ChargeSwitch Forensic DNA Purification kit.

Protocol 2 Protocol for preparing 1-10 µg DNA

| Step | Description |
|---|---|
| 1. | Swirl bottle with gel resin to obtain homogenous slurry |
| 2. | Pipette x µl gel slurry equal to 20 µl settled gel resin into tube or spin column |
| 3. | Remove storage solution by using magnetic rack or centrifugation (1 min. at 400 × g) |
| 4. | Add 400 µl equilibration buffer, mix and remove liquid |
| 5. | Add sample, 1-10 µg DNA in equilibration buffer e.g. 10 µl DNA (500 µg/ml) + 190 µl buffer |
| 6. | Incubate with occasional mixing for 5 minutes |
| 7. | Wash with 2 × 400 µl wash buffer/solution (remove liquid between steps) |
| 8. | Add 150 µl elution buffer, pipette resin slowly up and down a few times or vortex |
| 9. | Incubate with occasional mixing for 5 minutes |
| 10. | Recover eluate, measure DNA concentration and purity spectrophotometrically |

Equilibration buffer for polyCM and related resins: 1M glycine pH 2.0
Wash buffer/solution for polyCM and related resins: MilliQ water
Elution buffer for poly CM and related resins: 100 mM Tris pH 9.0

Protocol 3

| Step | Description |
|---|---|
| 1. | Add 200 µl 0.1M acetic acid to each tube. Vortex followed by brief centrifugation to settle beads. Remove supernatant. |
| 2. | Add 50 µl and 40 µl Salmon Sperm DNA (50 µg/ml) respectively. |
| 3. | Mix and incubate for 5 minutes. |
| 4. | Centrifuge and remove non-bound material. |
| 5. | Add 500 µl wash buffer (0.1M acetic acid), centrifuge to settle beads. Remove supernatant. |
| 6. | Repeat the wash step once. |
| 7. | Add 150 µl elution buffer to each tube (10 mM sodium hydroxide) and mix. Incubate for 5 minutes. |
| 8. | Centrifuge to settle beads. Recover the supernatant and measure DNA concentration. |

Results

Test of DNA Binding to Commercially Available Paramagnetic Beads

Two tubes containing 20 µl slurry (ChargeSwitch beads) and 200 µl purification buffer (supplied with the kit) were prepared. 50 µl and 40 µl Salmon Sperm DNA (50 µg/ml) were added to the tubes respectively. Purification was done according to protocol 1. Recovery according to UV-absorbance was 1.17 µg (35% of start material) and 1.06 µg (41% of start material) respectively.

Example 1

Test of DNA Binding to Prototype Resins

Screening of conditions for Poly CM Sepharose 6 FF

20 µl Poly CM gel slurry (gel media #8 at 50% slurry concentration) was added to two tubes.

Protocol 3 was used:
1. Add 200 µl 0.1 M acetic acid to each tube. Vortex followed by brief centrifugation to settle beads. Remove supernatant.
2. Add 50 µl and 40 µl Salmon Sperm DNA (50 µg/ml) respectively.
3. Mix and incubate for 5 minutes.
4. Centrifuge and remove non bound material.
5. Add 500 µl wash buffer (0.1 M acetic acid), centrifuge to settle beads. Remove supernatant.
6. Repeat the wash step once.
7. Add 150 µl elution buffer to each tube (10 mM sodium hydroxide) and mix. Incubate for 5 minutes.
8. Centrifuge to settle beads. Recover the supernatant and measure absorbance. If necessary, measure pH with pH paper.

Recovery according to UV-absorbance was 0.63 µg (19% of start material) and 0.48 µg (18% of start material) respectively. The pH of the supernatants was about pH 5. The pH determines ionization state of the poly CM ligand and should optimally be close to pH used in generic PCR buffers (between pH 8-9) after elution.

Replacing the elution buffer with 100 mM sodium hydroxide generated higher recovery (data not shown).

The poly CM resin acts as a buffer reservoir in itself and thus a different equilibration buffer was tested to reach an equilibration pH between pH 2-3. Four different buffers were tested in screening experiments:

| | |
|---|---|
| 1. glycine-buffer, pH 2.0 | 2. glycine-buffer, pH 3.0 |
| 3. acetate-buffer, pH 4.4 | 4. acetate-buffer, pH 5.0 |

The experiments were performed in spin columns and with varying equilibration/wash buffers according to protocol 2. 10 µl Salmon Sperm DNA was added (500 µg/ml) and eluted DNA was measured by absorbance. Results show that binding of DNA to the poly CM beads occur when the equilibration has been done below pH 4.4.

TABLE 2

Sonicated Salmon Sperm DNA (5 µg loaded) was isolated using different binding buffers.

| Tube | pH binding | DNA in wash | Eluted DNA recovery |
|---|---|---|---|
| 1 | 2.0 | 0.8 µg | 25% |
| 2 | 3.0 | 1.5 µg | 11% |
| 3 | 4.4 | 5.4 µg | 0% |
| 4 | 5.0 | 4.8 µg | 0% |

Example 2

Test of DNA Binding to Prototype Resins

Protocol 2 was used with glycine pH 2.0 as equilibration/wash buffer and 100 mM Tris pH 9.0 as elution buffer for various gel resins using DNA from Salmon Sperm and Calf Thymus.

TABLE 3A

Isolation of Salmon Sperm DNA on various gel resins containing different ligands. Binding was performed at pH 2.0.
Sample: Sonicated Salmon Sperm DNA, GEHC, 27-4565-01, 500 µg/ml
Amount DNA: 10 µg

| Gel media | DNA conc. In eluate | µg DNA eluted | A260/A280 | Recovery |
|---|---|---|---|---|
| 1, Carboxy Methyl Cellulose | 14.9 | 2.2 | 1.8 | 22% |
| 1, Carboxy Methyl Cellulose | 15.5 | 2.3 | 1.8 | 23% |
| 2, Cellulose sulfate | 10.5 | 1.58 | 1.7 | 16% |
| 3, Hydroxy Ethyl Cellulose | 2.6 | 0.4 | 1.7 | 4% |
| 3, Hydroxy Ethyl Cellulose | 6 | 0.9 | 1.7 | 9% |
| 4, Carboxy Methyl Dextran | 4.6 | 0.69 | 1.9 | 7% |
| 5, Poly CM | 4.8 | 0.72 | 1.7 | 7% |
| 8, Poly CM | 28.5 | 4.3 | 1.8 | 43% |
| 8, Poly CM | 36 | 5.4 | 1.8 | 54% |
| 9, Carboxymethyl | 37 | 5.6 | 1.8 | 56% |
| 9, Carboxymethyl | 37 | 5.6 | 1.9 | 56% |
| Charge Switch 40 µl | 10.2 | 1.5 | | 15% |

TABLE 3B

Isolation of Calf Thymus DNA on various gel resins containing different ligands. Binding was performed at pH 2.0.
Sample: Sonicated Calf Thymus DNA, GEHC, 27-4563-01, 500 µg/ml
Amount DNA: 10 µg

| Gel media | DNA conc. In eluate | µg DNA eluted | A260/A280 | Recovery |
|---|---|---|---|---|
| 2, Cellulose sulfate | 10 | 1.50 | 1.8 | 15% |
| 4, Carboxy Methyl Dextran | 5 | 0.75 | 2.0 | 8% |
| 5, Poly CM | 6.8 | 1.02 | 1.7 | 10% |
| 7, Sulfopropyl | 12.9 | 1.94 | 1.9 | 19% |
| 8, Poly CM | 28 | 4.20 | 1.9 | 42% |
| 9, Carboxymethyl | 3.1 | 0.47 | 2.2 | 5% |
| 10, Aminocaproic acid | 10.5 | 1.58 | 1.9 | 16% |
| Charge Switch 20 µl | 13.1 | 1.97 | 1.9 | 20% |
| Charge Switch 40 µl | 19.5 | 2.93 | 1.9 | 29% |

Example 3

Test of DNA Binding to Prototype Resins

Repeat the DNA binding experiments, but with the samples prepared in lysis buffer (from the ChargeSwitch kit). Mix samples by adding 3 ml lysis buffer, 30 µl proteinase K and 0.6 ml DNA (500 µg/ml). 100 µl samples were used for each gel resin. Protocol 2 is used with binding/washing at pH 2.0 and elution at pH 9.0 for prototype resins. Run according the user's manual for ChargeSwitch beads.

Results indicate that the lysis buffer contain something that interferes with DNA binding on the Poly CM Mag Sepharose low sub. and Poly CM Mag Sepharose high sub. Prototypes, (table 4).

TABLE 4

Samples containing water (blank samples) or DNA in lysis buffer were used to estimate background absorbance after elution.
Numbers are shown as the average of two samples measured at 260 nm.

| Gel media | water sample | Salmon Sperm DNA | Calf Thymus DNA |
|---|---|---|---|
| ChargeSwitch | 1.15* | 0.91 | 0.85 |
| 10, Aminocaproic acid | 0.06 | 0.05 | 0.05 |
| 5, Poly CM | 0.41 | 0.30 | 0.54 |
| 6, Poly CM | 3.10 | 3.01 | 2.68 |

*particulates in the eluate disturbed the UV-measurement.

A new lysis buffer was prepared, containing 1% Triton X-100 which was used in parallel with samples prepared with the ChargeSwitch kit. It was shown that Triton X-100 can bind to Poly CM Mag Sepharose high sub. when using the same protocol used for binding DNA. It is thus assumed that detergents based on polyoxyethylene moieties as in BRIJ, Triton and Tween will have the same ability to bind Poly CM gel resins under the same conditions used to bind DNA. The mechanism is not known, but a theory is that the binding involves hydrogen bonds.

TABLE 5A

Lysis buffer added to samples:
UV of non-adsorbed (flow-through) fluid

| | Lysis buffer (ChargeSwitch kit) | | Replicate 1 1% Triton X-100 | | Replicate 2 1% Triton X-100 | |
|---|---|---|---|---|---|---|
| Gel media | A260 | A280 | A260 | A280 | A260 | A280 |
| 10, Aminocaproic acid | 7.39 | 9.16 | 6.35 | 7.50 | 6.45 | 7.87 |
| 6, Poly CM | 1.32 | 3.07 | 1.41 | 3.25 | 1.42 | 3.33 |

TABLE 5B

Lysis buffer added to samples:
UV of bound and eluted material

| | Lysis buffer (ChargeSwitch kit) | | Replicate 1 1% Triton X-100 | | Replicate 2 1% Triton X-100 | |
|---|---|---|---|---|---|---|
| Gel media | A260 | A280 | A260 | A280 | A260 | A280 |
| 10, Aminocaproic acid | −0.01 | 0.00 | −0.01 | 0.00 | −0.01 | −0.01 |
| 6, Poly CM | 3.49 | 6.42 | 2.43 | 5.29 | 2.24 | 5.01 |

The bound detergent can be efficiently removed by washing the gel resins with buffer solutions containing organic solvents or pure organic solvent. For Poly CM Mag Sepharose high sub. an ethanol concentration of >30% improves the purity of bound DNA after purification compared with purely aqueous buffers. Binding of DNA in the presence of organic solvents give very poor recoveries.

TABLE 6

Binding of the UV absorbing detergent Triton X-100 to Poly CM Mag Sepharose high sub, followed by different wash steps including water or organic solvents.

| Gel media | non-adsorbed (flow-through) | | adsorbed (eluate) | | Residual |
|---|---|---|---|---|---|
| 6, Poly CM | A260 | A280 | A260 | A280 | Triton X-100 |
| water wash | 3.49 | 6.66 | 2.4 | 5.34 | 80% |
| water wash | 3.47 | 6.46 | 2.56 | 5.59 | 87% |
| wash 70% ethanol | 3.6 | 6.72 | 0.25 | 0.3 | 4% |
| wash 70% ethanol | 3.37 | 6.45 | 0.15 | 0.16 | 2% |
| wash methanol | 3.64 | 6.75 | 0.08 | 0.09 | 1% |
| wash methanol | 3.37 | 6.5 | 0.07 | 0.08 | 1% |

Figure 2:
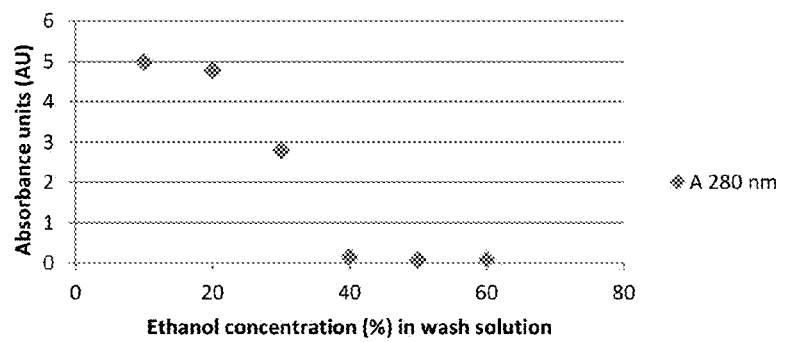
FIG. 2 is a diagram showing the effect of ethanol concentration in the wash step on the amount of residual Triton X-100 in eluted fractions.

In FIG. 2, Triton X-100 (100 µl, 1% (w/v)), was loaded on 20 µl of Poly CM Mag Sepharose high sub. followed by washing of the beads two times with 500 µl ethanol in water at various concentrations. The final UV absorbance (280 nm) was measured after elution. The UV absorbance in the various eluates is plotted against the ethanol concentration during the wash steps.

Test to bind 10 µg Salmon Sperm DNA on 20 µl resin or slurry in the presence of lysis buffer from the ChargeSwitch kit (Table 7). Wash solution was 40% ethanol in water for Poly CM resins.

TABLE 7

Comparison of DNA recovery from various poly CM Mag Sepharose prototypes when binding DNA in the presence of lysis buffer followed by wash with 40% ethanol.

| Gel media/Sample | A 260 | A280 | A260/A280 | DNA recovery |
|---|---|---|---|---|
| 7.5 µg DNA in Tris buffer | 1.12 | 0.58 | 1.93 | |
| ChargeSwitch | 1.04 | 0.56 | 1.86 | 93% |
| ChargeSwitch | 1.04 | 0.57 | 1.82 | 93% |
| 5, Poly CM Mag Sepharose low sub. | 0.15 | 0.11 | 1.36 | 13% |
| 5, Poly CM Mag Sepharose low sub. | 0.17 | 0.14 | 1.21 | 15% |
| 6, Poly CM Mag Sepharose high sub. | 0.31 | 0.22 | 1.41 | 28% |
| 6, Poly CM Mag Sepharose high sub. | 0.34 | 0.26 | 1.31 | 30% |

Test to bind DNA in the presence of (1% Tween 20 gave similar results compared with binding in the presence of Triton X-100 (data not shown).

TABLE 8

Comparison of DNA recovery from various poly CM Mag Sepharose prototypes when binding DNA in water without polyoxyethylene based detergents.

| Gel media/Sample | Wash sol. | Recovery DNA FT | Recovery DNA W1 | Recovery DNA Elu | A260/A280 Elu |
|---|---|---|---|---|---|
| Start material | | | | | 1.58 |
| ChargeSwitch | kit buffer | 13% | 19% | 51% | 1.68 |
| 5, Poly CM. | water | 128%* | 10% | 10% | 1.58 |

TABLE 8-continued

Comparison of DNA recovery from various poly CM Mag Sepharose prototypes when binding DNA in water without polyoxyethylene based detergents.

| Gel media/Sample | Wash sol. | Recovery DNA FT | Recovery DNA W1 | Recovery DNA Elu | A260/A280 Elu |
|---|---|---|---|---|---|
| 5, Poly CM. | 40% ethanol | 119%* | 77% | 6% | 1.54 |
| 6, Poly CM | water | 13% | 0% | 40% | 1.80 |
| 6, Poly CM | 40% ethanol | 17% | 16% | 53% | 1.75 |

*Particluates in the flow-through disturbed the UV-measurement.

DNA and non-ionic detergents (polyoxyethylene based) binds to poly CM immobilized gel media at pH 2-3. Detergents like Triton X-100 competes with DNA for binding sites, giving lower yield of DNA in eluate, however the detergents can be washed away by using wash solution containing >30% ethanol or methanol. Both DNA and detergents are prevented to bind to poly CM resins in the presence of ethanol at concentrations above 30%. Bound detergents can be washed away by using various levels of organic solvent on the wash buffers/solutions. Lysis buffer containing SDS (sodium dodecylsulfate) is recommended when no loss of capacity of the gel media is wanted.

Example 4

Binding of gDNA from Complex Samples 1.2 g (wet) cell paste from centrifugation of $89.5 \times 10^6$ cells (mammalian CHO cells), was extracted with a buffer containing 10 mM Tris, pH 9.0+5 mM EDTA+0.5% SDS. 10 µl proteinase K (Invitrogen ChargeSwitch kit) was added per ml lysis solution (89.5 µl proteinase K solution was added to 8.95 ml cell extract). After incubation at 58° C. (to allow cleavage of proteins) the extract was clarified by centrifugation.

ChargeSwitch beads were used according to instructions from the user manual. Poly CM Mag Sepharose low sub. and Poly CM Mag Sepharose high sub. were prepared according to protocol 2, except for the addition of equilibration buffer. 20 µl of 2 M glycine pH 2.0 was added prior to sample application to Poly CM resins. 900 µl 5 mM glycine pH 2.0 was added during sample application, (100 µl of the cell extract was added to the 20 µl of beads (or ChargeSwitch slurry). After incubation for 5 minutes at room temperature, the beads were washed with 2×500 µl $H_2O$ (Poly CM gel media) or with wash buffer (ChargeSwitch). Elution of Poly CM gels were done with 150 mM Tris pH 9.0 buffer.

There was a large difference in UV absorbance at 230 nm between the different eluates (A230 nm shows organic content). Highest A230 nm absorbance was found in eluates from the ChargeSwitch beads. The purity was only within the 1.7-2.0 limits for Poly CM Mag Sepharose high sub. whereas the yield was highest for the ChargeSwitch beads. The difference in the design of the beads may partly explain the difference in capacity. The ChargeSwitch beads are based on solid beads with a diameter of 1 µm. The base matrix of Poly CM Mag Sepharose beads are porous with a diameter of 50 µm. Large molecules like genomic DNA is probably bound primarily to the surface of the particles. The surface area for the ChargeSwitch beads used in this experiment was about 12 $dm^2$ whereas the surface area for the Poly CM resins were 2,4 $dm^2$. A five-fold difference in surface area. The different chemistry of the beads may also be an important factor for the binding capacity. Despite a five-fold larger surface area, the ChargeSwitch beads have only 46% higher recovery (or about 1.5-fold). When binding molecules in batch mode (like these experiments), the needed capacity is modulated by amount of resin used. Therefore, the gDNA capacity of 20 μl of ChargeSwitch bead slurry is equivalent to 29 μl of Poly CM high sub. and 35 μl of Poly CM low sub. In another way, the capacity of Poly CM high sub. for gDNA from CHO cells is about 0.44-0.60 μg/dm2 or 55-65 μg gDNA/ml settled beads.

TABLE 9

Recovery and purity of DNA isolated from
89.5 × 10⁶ cells (CHO-cells) using various gel media.

| Gel media | Purity (A260/A280) | DNA yield (μg) | A260/A230 |
|---|---|---|---|
| ChargeSwitch | 1.58 | 3.2 | 0.54 |
| 5, Poly CM | 1.54 | 1.0 | 0.53 |
| 6, Poly CM | 1.95 | 1.4 | 1.26 |

Example 5

Binding of Residual DNA (Host Cell DNA) from MDCK Cells, after Purification of Virus Particles Host cell DNA in samples containing purified virus particles is routinely analyzed by running qPCR analysis on a target gene. Levels in some sample specimens may go from 50 μg/ml down to μg/ml levels. 30 μl of a reference sample (standard) containing 50 μg/ml host cell DNA (1.5 μg total DNA), was bound to Poly CM Mag Sepharose low sub., Poly CM Mag Sepharose high sub. or to ChargeSwitch beads respectively according to the modified protocol 2 (see CHO cell experiment, example 4).

TABLE 10

Quantification of DNA using qPCR. Samples derived from a virus purification process containing residual host cell DNA from MDCK cells. Recovery to 20 μl settled gel was determined (poly CM gel media) or to 20 μl gel slurry (ChargeSwitch).

| Gel media | DNA Conc. qPCR (ng/ml) | CV (%) | DNA recovery (μg) |
|---|---|---|---|
| 5, Poly CM | 1313 | 46.6 | 0.20 |
| 5, Poly CM | 1237 | 5.2 | 0.19 |
| 6, Poly CM | 3414 | 7.5 | 0.51 |
| 6, Poly CM | 2058* | 9.6 | 0.31 |
| ChargeSwitch | 3467 | 2.9 | 0.52 |
| ChargeSwitch | 3373 | 3.7 | 0.51 |

*mixing by pipet led to loss of beads.

The Poly CM Mag Sepharose high sub. resins were sticky after binding of DNA and in one of the samples some loss of DNA was noticed due to pipetting. The other sample was mixed with vortex. Both Poly CM Mag Sepharose high sub. and ChargeSwitch beads bound 0.5 μg DNA according to the qPCR analysis (table 12), whereas Poly CM Mag Sepharose low sub. bound 0.2 μg of DNA. This corresponds to a capacity of 10-25 μg DNA/ml Poly CM resin and about 25 μg DNA/ml slurry (ChargeSwitch). The size distribution of the DNA from these samples is not known, but it may be a mixture of DNA strands from smaller to larger fragments.

Discussion

The examples show that DNA can be isolated using poly CM ligands (polyacrylic acid), immobilized on agarose based beads. Best results occur when binding at pH between 2.0-3.0 in the presence of a lysis buffer that does not contain polyoxyethylene based detergents and organic solvents at a concentration of less than 30%. The estimated capacity for poly CM Mag Sepharose high sub. is between 25-270 μg DNA per ml of resin, depending on the source of the material and protocol used. Other polymer ligands also show DNA binding properties, such as carboxy methyl cellulose and carboxy methyl dextran.

The invention claimed is:

1. A method for purification of nucleic acid comprising:
   adding a sample comprising a nucleic acid to a polymer having neutral charge;
   reversibly binding said nucleic acid to said polymer by hydrogen bonding under pH conditions <5 in the presence of a binding solution that does not contain polyoxyethylene based detergents;
   washing said polymer with a washing solution; and
   eluting said nucleic acid from said polymer under conditions of pH >5.

2. The method of claim 1, wherein the polymer is polycarboxylated.

3. The method of claim 1, wherein the polymer comprises 100-500 monomer units.

4. The method of claim 1, wherein the polymer is polyacrylic acid, poly lactic acid or carboxymethyldextran.

5. The method of claim 1, wherein polymers are used as ligands attached to a natural or synthetic solid phase or matrix, such as a bead, particle, membrane, filter, chip, sensor chip, for example a SPR chip, monolith, microfluidic device, pipette tip or any other surface.

6. The method of claim 5, wherein the solid phase comprises magnetic beads.

7. The method of claim 5, wherein the solid phase comprises a filter.

8. The method of claim 1, wherein the binding of nucleic acid occurs at pH 1-5, preferably pH 2-4, and elution occurs at pH 5-14, preferably pH 7-10.

9. The method of claim 1, wherein the nuclei acid is amplified, such as by PCR, directly after elution.

10. The method of claim 1, wherein the sample comprises nucleic acids of different sizes and thus different hydrogen bonding strength which are separated from each other by adding a solution or flow of a medium affecting hydrogen bonding.

11. The method of claim 1, wherein the eluted nucleic acids are larger than 200 bp.

12. The method of claim 1, wherein the eluted nucleic acids are 10-40 kb and are used for PCR applications.

13. The method of claim 1, wherein the eluted nucleic acids are directly sequenced after elution (without amplification).

14. The method of claim 1, wherein the nucleic acid is used for vaccine applications.

15. The method of claim 1, wherein the binding solution contains organic solvents at a concentration of less than 30%.

16. The method of claim 1, wherein the washing solution contains organic solvents, or is a pure organic solvent.

17. The method of claim 15, wherein the washing solution comprises an organic solvent at a concentration >30%.

18. The method of claim 17, wherein said organic solvent is ethanol.

* * * * *